(12) United States Patent
Harrison et al.

(10) Patent No.: US 6,224,830 B1
(45) Date of Patent: May 1, 2001

(54) ABSORBANCE CELL FOR MICROFLUID DEVICES

(75) Inventors: D. Jed Harrison, Edmonton; Graham H. McKinnon, Beaumont; Nghia H. Chiem, Edmonton; Gregor Ocvirk, Edmonton; Hossein Salimi-Moosavi, Edmonton; Yutao Jiang, Edmonton, all of (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/016,142

(22) Filed: Jan. 30, 1998

(51) Int. Cl.[7] .................................................. G01N 21/01
(52) U.S. Cl. ...................... 422/82.11; 422/81; 422/82.05; 422/82.09; 204/603; 204/612; 356/73.1; 356/246; 356/344
(58) Field of Search ............................. 422/82.11, 82.09, 422/82.05, 81; 356/51, 73.1, 344, 246; 204/452, 453, 461, 603, 604, 612

(56) References Cited

U.S. PATENT DOCUMENTS

| | | | |
|---|---|---|---|
| 4,376,641 | * | 3/1983 | Nestrick et al. . |
| 4,529,614 | | 7/1985 | Burns . |
| 4,608,344 | * | 8/1986 | Carter et al. ...................... 422/82.11 |
| 4,675,095 | * | 6/1987 | Kambara et al. ..................... 356/344 |
| 4,680,201 | * | 7/1987 | Hjerten . |
| 4,816,123 | | 3/1989 | Ogan et al. . |
| 4,891,120 | | 1/1990 | Sethi et al. . |
| 4,908,112 | | 3/1990 | Pace . |
| 4,963,498 | * | 10/1990 | Hillman et al. . |
| 5,015,350 | * | 5/1991 | Wiktorowicz . |
| 5,059,396 | * | 10/1991 | Opitz et al. ......................... 422/82.11 |
| 5,074,982 | * | 12/1991 | Novotny et al. . |
| 5,082,629 | * | 1/1992 | Burgess, Jr. et al. .............. 422/82.11 |
| 5,110,439 | | 5/1992 | Holloway . |

(List continued on next page.)

FOREIGN PATENT DOCUMENTS

| | | |
|---|---|---|
| 0396163A2 | 3/1990 | (EP) . |
| 0597152A1 | 11/1992 | (EP) . |
| 0597552A1 | 11/1993 | (EP) . |
| 0762119A1 | 9/1995 | (EP) . |
| 0770871A2 | 9/1996 | (EP) . |
| 0840113A2 | 10/1997 | (EP) . |
| WO95/24632 | 3/1995 | (GB) . |
| WO93/08903 | 11/1992 | (NL) . |

(List continued on next page.)

OTHER PUBLICATIONS

Signal–to–noise ratio analysis in laser absoprtion spectrometers using optical multipass cells. Peter Werle and Franz Slemr. Applied Optics vol. 30, No. 4, pp. 430–434, Feb. 1, 1991.*

(List continued on next page.)

*Primary Examiner*—Jan Ludlow
(74) *Attorney, Agent, or Firm*—Christensen O'Connor Johnson Kindness PLLC

(57) ABSTRACT

An improved absorbance or detection cell for a microfluid device, and in accordance with an aspect of the invention, the absorbance cell comprises a bottom plate having a channel bearing surface in which a channel having a fluid inlet and fluid outlet is defined, a top plate having a channel facing surface bound to the channel bearing surface of the bottom plate and first and second reflecting elements formed on opposed sides of the channel to form a waveguide through which the channel extends such that radiation propagating along the waveguide makes multiple passes across the channel, the waveguide having a radiation input end and a radiation output end.

91 Claims, 10 Drawing Sheets

U.S. PATENT DOCUMENTS

| | | |
|---|---|---|
| 5,132,012 | 7/1992 | Miura et al. . |
| 5,181,999 * | 1/1993 | Wiktorowicz . |
| 5,192,406 | 3/1993 | Woolley . |
| 5,194,133 | 3/1993 | Clark et al. . |
| 5,239,360 | 8/1993 | Moring et al. . |
| 5,250,263 * | 10/1993 | Manz ................................. 422/81 |
| 5,273,633 | 12/1993 | Wang . |
| 5,274,227 | 12/1993 | Moring . |
| 5,304,487 * | 4/1994 | Wilding et al. . |
| 5,322,608 | 6/1994 | Karger et al. . |
| 5,414,508 | 5/1995 | Takahashi et al. . |
| 5,415,747 * | 5/1995 | Holloway . |
| 5,462,646 * | 10/1995 | Shieh . |
| 5,498,392 * | 3/1996 | Wilding et al. . |
| 5,500,071 | 3/1996 | Kaltenbach et al. . |
| 5,502,169 * | 3/1996 | Schomburg et al. . |
| 5,554,339 * | 9/1996 | Cozzette et al. . |
| 5,571,410 | 11/1996 | Swedberg et al. . |
| 5,572,328 | 11/1996 | Fouckhardt et al. . |
| 5,580,435 | 12/1996 | Kovacs . |
| 5,585,069 * | 12/1996 | Zanzucchi et al. . |
| 5,599,503 | 2/1997 | Manz et al. . |
| 5,605,613 * | 2/1997 | Shieh . |
| 5,632,957 * | 5/1997 | Heller et al. . |
| 5,635,358 | 6/1997 | Wilding et al. . |
| 5,637,469 | 6/1997 | Wilding et al. . |
| 5,641,400 | 6/1997 | Kaltenbach et al. . |
| 5,644,395 | 7/1997 | Folta . |
| 5,645,702 | 7/1997 | Witt et al. . |
| 5,646,039 | 7/1997 | Northrup et al. . |
| 5,658,413 | 8/1997 | Kaltenbach et al. . |
| 5,665,216 * | 9/1997 | Karger et al. . |
| 5,691,205 * | 11/1997 | Kawabata et al. ................. 422/82.11 |
| 5,699,157 | 12/1997 | Parce . |
| 5,757,482 | 5/1998 | Fuchs et al. . |
| 5,766,957 * | 6/1998 | Robinson et al. ................. 422/82.11 |
| 5,792,943 | 8/1998 | Craig . |
| 5,804,022 | 9/1998 | Kaltenbach et al. .................. 156/257 |
| 5,815,258 * | 9/1998 | Nakanishi ............................ 356/246 |

FOREIGN PATENT DOCUMENTS

WO 91/10122 * 7/1991 (WO) .
WO 94/28395 * 12/1994 (WO) .

OTHER PUBLICATIONS

Microfabrication of a Planar Absorbance and Fluorescence Cell for Integrated Capillary Electrophoresis Devices. Zhenhua Liang, Nghia Chiem, Gregor Ocvirk, Thompson Tang, Karl Fluri, and D. Jed Harrison. Analytical Chemistry vol. 68 No. 6, Mar. 15, 1996. pp. 1040–1046.

Miniaturization of Separation Techniques Using Planar Chip Technology, Andreas Manz, Elisabeth Verpoorte, Carlo S. Effenhauser, Norbert Burggraf, Daniel E. Raymond, D. Jed Harrison and H. Michael Widmer, JOurnal of High Resolution Chromatograhy, vol. 16, Jul. 1993, p. 433–436.

Z–Shaped Flow Cell for UV Detection in Capilary Electrophoresis, J.P. Chervet, R.E.J. Van Soest and M. Ursem, Journal of Chromatography, 543 (1991), 439–449.

A silicon flow cell for optical detection in miniaturized total chemical analysis systems, E. Verpoorte, A. Manz, H. Ludi, A.E. Bruno, F. Maystre, B. Krattiger and H.M. Widmer, B.H. vanderSchoot and N.F. de Rooij, Sensors and Actuators B., 6(1992) 66–70.

Optimization and evaluation of the performance of arrangements for UV detection in high–resolution separations using fused–silica capillaries, G.J.M. Bruin, G. Stageman, A.C. Van Asten, X. Xu, J.C. Kraak and H. Poppe, Journal of Chromatography, 559(1991) 163–181.

Flow Dependence and Sensitivity of the Refractive Index Gradient Measurement with the Z–Configuration Flow Cell at Low Reynolds Number, Darrell O. Hancock, Curtiss N. Renn, and Robert E. Synovec, Anal. Chem. 1990, 62, 2441–2447.

Axial–Beam On–Column Absorption Detection for Open Tubular Capillary Liquid Chromatography, Anal. Chem. 1990, 62, 1580–1585.

Instrumentation, Ultra–Sensitive UV Detection in Micro Separation, J.P. Chervet, M. Ursem, and J.P. Salzmann, R.W. Vannoort, Journal of High Resolution Chromatography, vol. 12, May 1989, p. 278–281.

On–Column Capillary Flow Cell Utilizing Optical Waveguides for Chromatographic Application, Alfredo E. Bruno, Ernst Gassmann, Nico Pericles and Klaus Anton, Anal. Chem. 1989, 61, 876–883.

Construction and Use of Reflecting Multiple–Pass Absorption Cells for the Ultraviolet, Visible, and Near Infrared, John H. Could, Applied Spectroscopy, vol. 25, No. 1, 1971, p. 103–105.

Technical Notes, Rectangular Capillaries for Capillary Zone Electrophoresis, Takao Tsuda, Jonathan V. Sweedler, and Richard N. Zare, Anal. Chem. 1990, 62, 2149–2152.

On–Column UV Absorption Detector for Open Tubular Capillary Zone Electrophoresis, Yvonne Walbroehl and James W. Jorgenson, J. Chronology, 1984, 135–143.

Waveguides as Chemical Sensors, Raymond E. Dessy, Analytical Chemistry, vol. 61, No. 19, Oct. 1, 1989, 1079–1094.

Optical Improvements of a Z–Shaped Cell for High–Sensitivity UV Absorbance Detection in Capillary Electrophoresis, Stephen E. Moring and Richard T. Reel, Remco E.J. van Soest, Anal Chem. 1993, 65, 3454–3459.

Sensitivity Enhancement for Capillary Electrophoresis, Michael Albin, Paul D. Grossman, and Stephen E. Moring, Analytical Chemistry, vol. 65, No. 10, May 15, 1993, 489–497.

Nanoliter–Scale Multireflection Cell for Absorption Detection Capillary Electrophoresis, Tiansong Wang, Joseph H. Aiken, Carmen W. Huie, and Richard A. Hartwick, Anal. Chem. 1991, 63, 1372–1376.

A Long Path Gas Absorption Cell, Robert G. Pilston, John U. White, Journal of the Optical Society of America, vol. 44, No. 7, p. 572–573. 1954.

Long Optical Paths of Large Aperture, John U. White, J.O.S.A., vol. 32, May, 1942, p. 285–288.

Long–Path Infrared Spectrocopy For Air Pollution Research, Edgar R. Stephens, Applied Spectroscopy, No. 3, 1958, p. 80–84.

Axis Paths in Spherical Mirror Interferometers, Herriott, H. Kogelnik, and R. Kompfner, Applied Optics, vol. 3, No. 4, Apr. 1964, p. 523–526.

Folded Optical Delay Lines, Donald R. Herriott and Harry J. Schulte, Applied Optics, vol. 4, No. 8, Aug. 1965, p. 883–889.

* cited by examiner

FIG. 3D
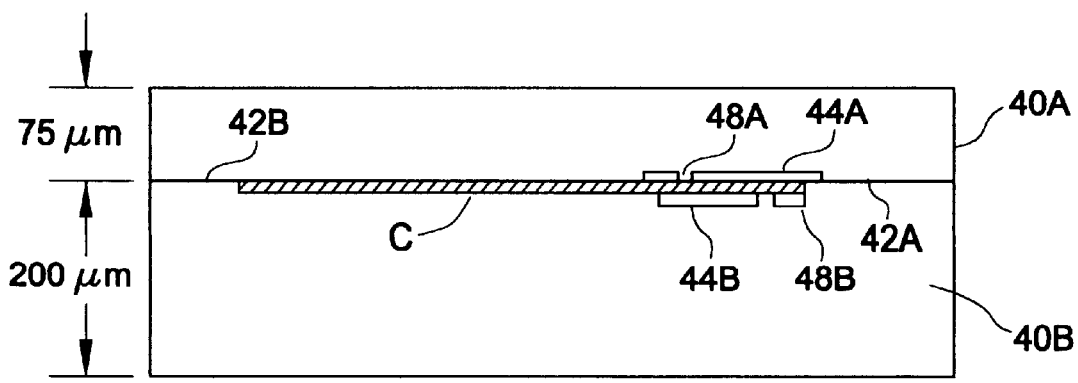
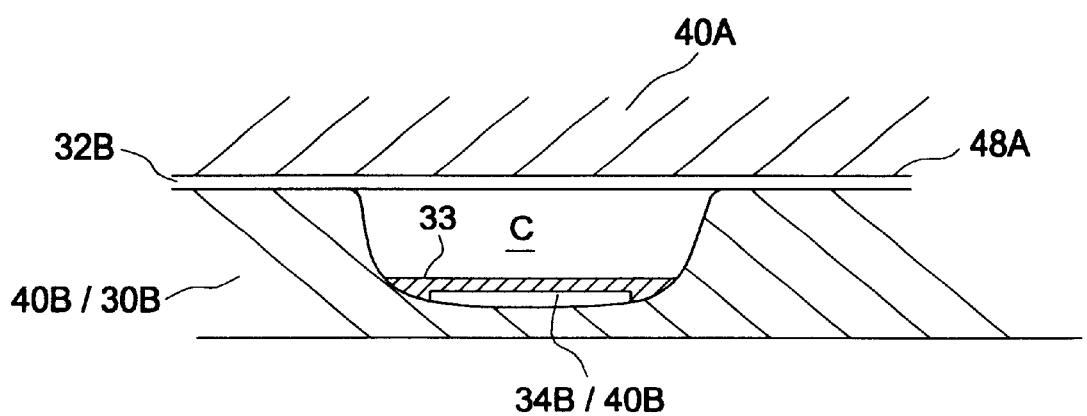
FIG. 3E

ABSORBANCE CELL FOR MICROFLUID DEVICES

FIELD OF THE INVENTION

This invention relates to microfluid total analysis systems, and methods for making such systems.

BACKGROUND OF THE INVENTION

Obtaining good limits of detection when using optical detection has been a challenge in capillary electrophoresis, due to the short path lengths engendered by the small capillary diameter. Increasing the path length of measuring radiation with a detection zone is therefore desirable. Several approaches are known in the art, such as the U-channel described in "Microfabrication of a Planar Absorbance and Fluorescence Cell for Integrated Capillary Electrophoresis Devices", Zhenhua Liang et al, Analytical Chemistry, vol. 68, no. 6, Mar. 15, 1996, the Z-channel described in European patent application 93203166.9 published May 18, 1994, or an in-channel reflection device in silicon, described in Manz et al, U.S. Pat. No. 5,599,503 issued Feb. 4, 1997.

The U-channel device of Liang et al has the disadvantage that, although it is of simple design, it is hard to manufacture since an optic fiber used to deliver light to the absorbance zone must have a dimension similar to the size of the channel. Sliding such a fiber into a hole in the device is a very difficult task.

In the design of absorbance cells in microfluid devices, it is desirable to reduce the loss of resolution due to the detector volume. Greater detector volume means lower resolution. This arises as follows. If the absorbance zone becomes very long (higher volume), any molecules that absorb the measuring radiation in the entire path length of the absorbance zone are detected. Thus, if the separation of two species of molecules being detected is less than the length of the absorbance zone the signals from the two species overlap and cannot be resolved. The detector length in a microfluid device is limited to about 200 $\mu$m.

Manz et al, who apply principles known from 1942 (White, J. Opt. Soc. Am., 32 (1942) 285) attempt to solve this problem for certain devices by reflecting light off bounding surfaces of a channel, but the disclosed device is not readily manufactured in devices other than silicon and cannot be used very easily for capillary electrophoresis due to the use of the semiconductor silicon. The formation of mirror planes in glass at the sample introduction point is particularly hard to achieve. Other difficulties include alignment difficulty resulting from the use of optical fibers, and the necessity of forming holes through the plates defining the channel. It is an object of this invention to provide a microfluid device with enhanced path length, improved sensitivity, that may be manufactured without great difficulty in a wide variety of materials.

SUMMARY OF THE INVENTION

There is therefore provided an improved absorbance or detection cell for a microfluid device, and in accordance with an aspect of the invention, the absorbance cell comprises a bottom plate having a channel bearing surface in which a channel is defined, the channel having a fluid inlet and fluid outlet, a top plate having a channel facing surface bound to the channel bearing surface of the bottom plate and first and second reflecting elements formed on opposed sides of the channel to form a waveguide through which the channel extends such that radiation propagating along the waveguide makes multiple passes across the channel, the waveguide having a radiation input end and a radiation output end.

According to a further aspect of the invention, electrically non-conducting material of one of the top plate and bottom plate is disposed between the first reflecting element and the channel, the electrically non-conducting material being transparent to measuring radiation. By this aspect, the reflecting element is no longer in contact with buffer solution during analysis, the device becomes easier to manufacture and in addition the reflecting elements may be made laterally extensive to block stray radiation from reaching a detector.

According to a further aspect of the invention, electrically non-conducting material of the top plate is disposed between the first reflecting element and the channel.

According to a further aspect of the invention, electrically non-conducting material of the bottom plate is disposed between the second reflecting element and the channel, the electrically non-conducting material of the bottom plate being transparent to measuring radiation.

According to a further aspect of the invention, the waveguide input end and the waveguide output end are arranged so that measuring radiation enters the waveguide through one of the top plate and the bottom plate and exits the waveguide through the other of the top plate and the bottom plate. By this arrangement, contamination of detected radiation from radiation at the input end of the waveguide is reduced.

According to a further aspect of the invention, the first reflecting element is formed on a first face of a first plate segment, the first face of the first plate segment abuts against a second face of a second plate segment, and together the first and second plate segments form the bottom plate. By this arrangement, the path length of measuring radiation in the bottom plate is reduced.

According to a further aspect of the invention, there is also provided an input aperture in one of the first and second reflecting elements for introduction of measuring radiation into the waveguide, and an output aperture in the other of the first and second reflecting elements for egress of measuring radiation from the waveguide.

According to a further aspect of the invention, the waveguide input end is arranged such that radiation introduced into the waveguide through one of the top plate and bottom plate propagates at an angle $\alpha$ to a normal to the reflecting surfaces as the radiation passes through the one of the top plate and bottom plate by this arrangement, it is not necessary to have a reflecting surface within the waveguide that deflects perpendicular incident light along the waveguide.

According to a further aspect of the invention, the waveguide input end is arranged such that radiation introduced to the waveguide has a free space mode of propagation. Radiation with a free space mode of propagation advantageously allows control of the radiation propagation direction using optical elements such as mirrors and lenses.

According to a further aspect of the invention, the reflecting elements extend laterally to form a shield between a measuring radiation source and a measuring radiation detector.

According to a further aspect of the invention, the channel of a microfluid device used for capillary electrophoresis is coated with polysiloxane.

According to a further aspect of the invention, the fluid inlet of a microfluid device comprises a flat ended capillary inserted through a hole in a first plate, with the flat ended capillary butting up against a surface of a second plate in which a channel is defined with the flat ended capillary centered over the channel.

According to further aspects of the invention, there are provided several methods of making an absorbance cell for a microfluid device.

One such method comprises the steps of providing a channel in a first plate, attaching a second plate to the first plate; and forming a waveguide about the channel with material of one of the first plate and second plate between the waveguide and the channel.

Another such method comprises the steps of:
forming a first reflecting element on a first face of a first bottom plate segment;
bonding a second bottom plate segment to the first face of the first bottom plate segment;
forming a channel in the second bottom plate segment on a side of the second bottom plate segment opposed to the first bottom plate segment;
bonding a top plate to the first bottom plate segment; and
forming a second reflecting element on the top plate, the first and second reflecting elements being formed on opposed sides of the channel to form a waveguide through which the channel extends such that radiation propagating along the waveguide makes multiple passes across the channel, the waveguide having a radiation input end and a radiation output end.

In another aspect of the invention, there is provided a method of making an absorbance cell for a microfluid device, the method comprising the steps of:
forming a first reflecting element on a first bottom plate segment;
bonding a second bottom plate segment to the first bottom plate segment by heat treating the first and second bottom plate segments with the first reflecting element disposed between the first and second bottom plate segments;
forming a channel in the second bottom plate segment;
bonding a top plate to the second bottom plate segment; and
forming a second reflecting element on the top plate, the first and second reflecting elements being formed on opposed sides of the channel to form a waveguide through which the channel extends such that radiation propagating along the waveguide makes multiple passes across the channel, the waveguide having a radiation input end and a radiation output end.

In a preferred manner of implementing an aspect of the method of the invention in which the plates are heat treated, the top and bottom plate segments are made of glass and are heated to a temperature of just below the glass softening temperature, preferably about 400° C. to about 500° C.

These and other aspects of the invention are described in the detailed description of the invention and claimed in the claims that follow.

BRIEF DESCRIPTION OF THE DRAWINGS

There will now be described preferred embodiments of the invention, with reference to the drawings, by way of illustration only and not with the intention of limiting the scope of the invention, in which like numerals denote like elements and in which:

FIG. 3D is a cross-section through a fourth device according to the invention;

FIG. 3E shows a section through the design of FIG. 3D;

DETAILED DESCRIPTION OF PREFERRED EMBODIMENTS

Figure 1:
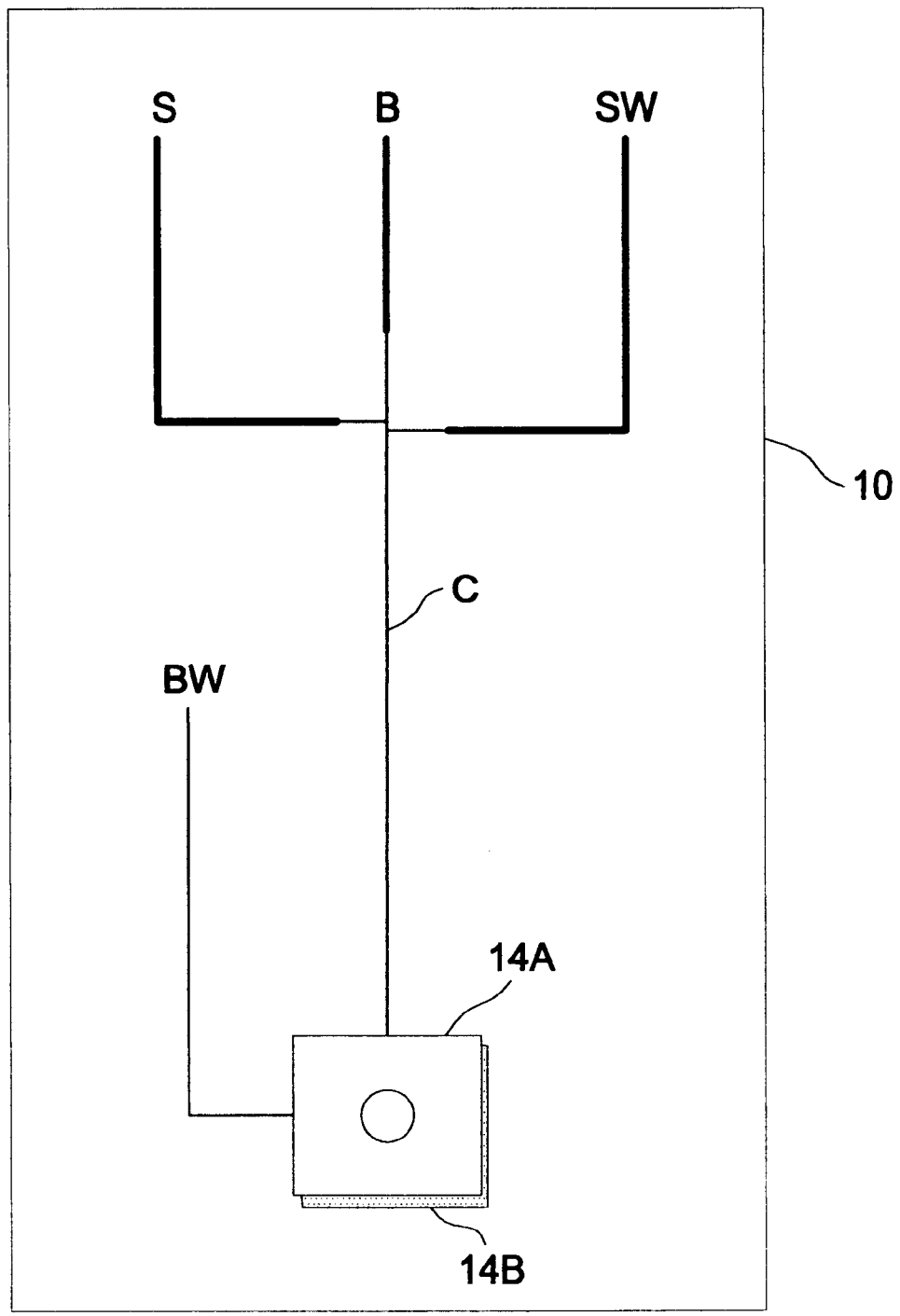
FIG. 1 is a top view of a total analysis system incorporating an aspect of the invention.

The absorbance cell of the present invention is intended for use with a sample delivery cell of the type illustrated in FIG. 1. Reservoirs S, B, SW and BW and channel C may all be formed on a substrate 10 according to principles well known in the art, such as described in Anal. Chem., vol. 68, no. 6, pp. 1040–1046 or U.S. Pat. Nos. 5,571,410 (Nov. 5, 1996) and 5,571,410 (Jul. 8, 1997). The channel C should have a height of about 20–30 $\mu$m and similar width or slightly larger since the etching process tends to make a flat bottomed channel. The configuration shown is suitable for electrophoresis. Various other configurations of channels and reservoirs may be used according to the analytical method being used. Analytical methods for which the present system is applicable include electrophoresis, chromatography, supercritical fluid chromatography and fluid injection analysis. In the present system, a sample to be analyzed may be injected from reservoir S into channel C by application of a electrical potential between S to SW. A buffer fluid is injected into the channel C from reservoir B. The sample to be analyzed is separated by application of a an electrical potential from B to BW. Reservoirs S and B function as inlets for channel C, while Bw is an outlet for channel C.

The present invention provides an absorbance cell for the microfluid device shown in FIG. 1 in which the sample being measured is detected within the cell. The absorbance cell may be placed on a separate substrate from the injection cell, but it is preferable that both be housed on the same substrate.

Figure 2:
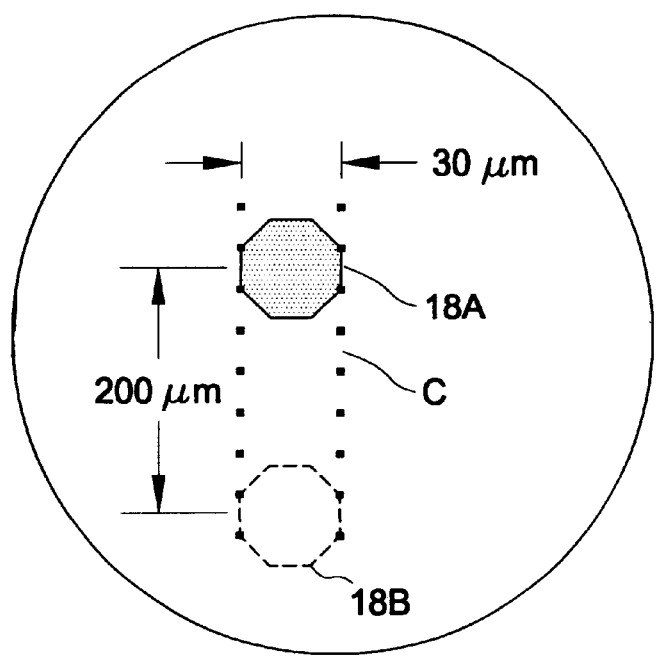
FIG. 2 is an enlargement of a portion of the device of FIG. 1.
Figure 3A:
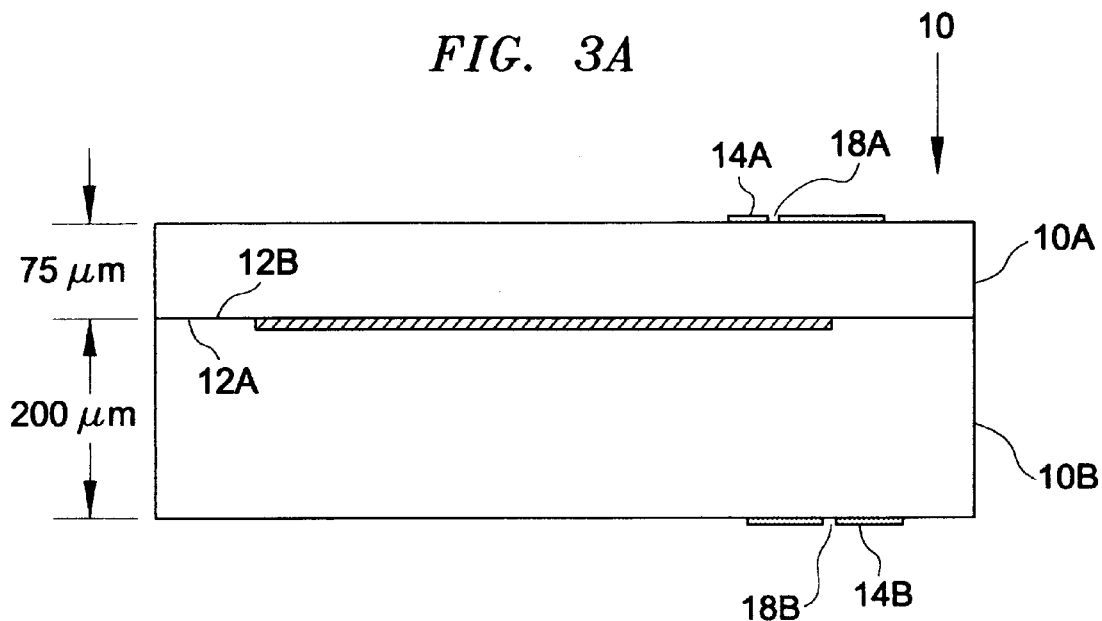
FIG. 3A is cross-section through a first device according to the invention.

Referring to FIGS. 2 and 3A, an absorbance cell according to the invention has a bottom plate 10B and top plate 10A. Bottom plate 10B has a channel bearing surface 12B in which channel C is defined. The top plate 10A has a channel facing surface 12A bound to the channel bearing surface 12B of the bottom plate 10B. The top plate 10*a* and bottom plate 10*b* are preferably laterally extensive to act as a shield for radiation from the waveguide input end contaminating radiation sensed by the detector. The reflecting elements 14A and 14B are desirably a square of 2 centimeters on each side, since this lateral extension gives good protection from scattered light to a photodiode detector, which may itself have a mm or larger sized detection region. By comparison, the waveguide may be in the order of 200 $\mu$m long. The reflecting elements should at least have an area that is sufficient to cover the detection region of the detector.

Various methods may be used to bind the top plate 10A to the bottom plate 10B, such as heat treating, cold bonding, clamping and adhesive, depending on the design of the absorbance cell. Heat treating is desirable where the components will not be damaged by the application of heat. For example, heat treating may be used with the designs of FIGS. 3A and 3B. For designs in which silicon is used as the substrate material, adhesive or clamping may be used. If the device is to be used for electrophoresis, metal clamps may cause problems and plastic clamps should be used. In cold bonding, the channel bearing surface 12B and channel facing surface 12A should be ground and polished, then cleaned with a high pressure rinse to blow off any remaining particulate. Application of pressure at room temperature may then adequately bond the top plate to the bottom plate. Slightly elevated temperature, for example up to 100° C. may also be used to improve the bond, or even higher temperatures below the glass softening temperature, for example 400° C.–500° C. (preferably 450° C.) for times from 2 minutes to an hour, preferably about 30 min. in the case of such glasses as Crown™ glass 0211 or Pyrex™ from Corning of New York, or Borofloat™ available from Schott. These bonding techniques may also be used on the designs shown in FIGS. 3B, 3C and 3D. However, the design of the device may dictate that one technique is preferred for that device.

Figure 5:
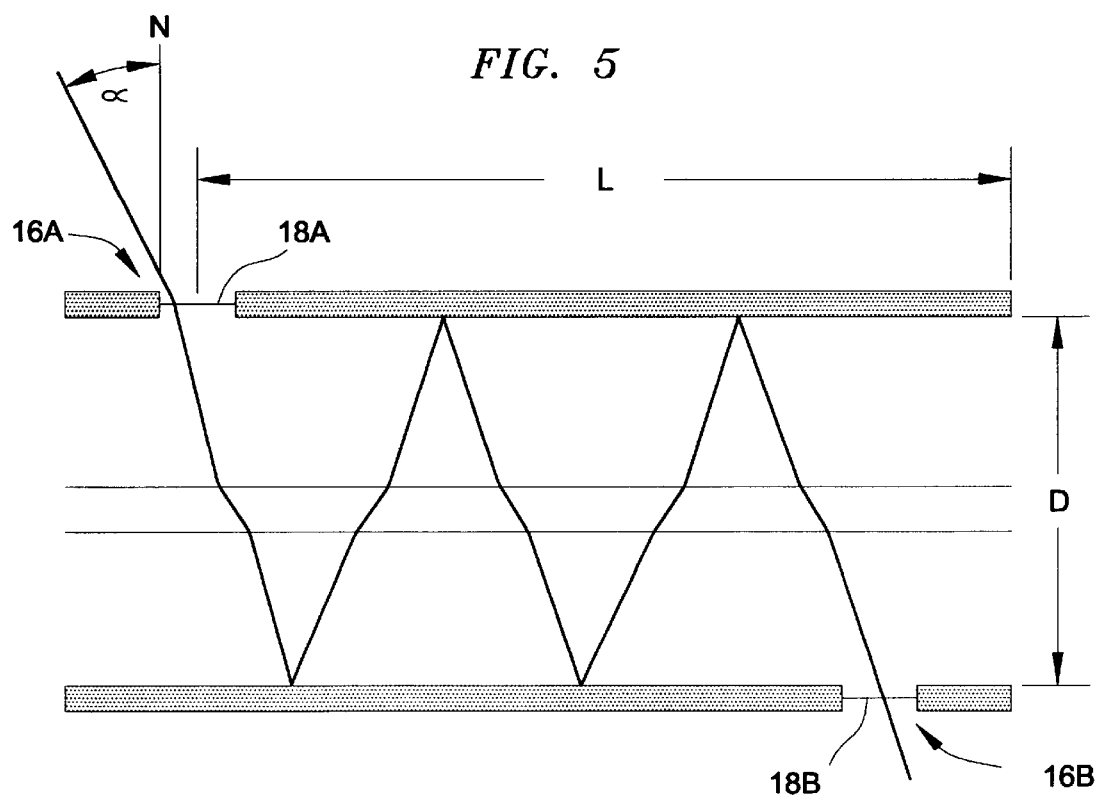
FIG. 5 is a cross-section through an absorbance cell showing propagation of measuring radiation within the waveguide.

Reflecting elements 14A and 14B are formed on opposed sides of the channel C to form a waveguide through which the channel C extends. As shown in FIG. 5, radiation propagating along the waveguide makes multiple passes across the channel C. The waveguide has a radiation input end 16A and a radiation output end 16B. The reflecting elements 14A and 14B form mirrors whose reflectivity depends on the material used for the mirrors. Aluminum (R=95%, about 1000 Angstroms thick) may be used, and also other metals such as platinum and tungsten which give higher reflectivity but at greater cost. In addition, dielectric 99.5% reflectivity quarter wave plates made of for example calcium fluoride may be used if the bonding process used to bond top and bottom plates is not carried out at such a high temperature that delamination of the reflecting element occurs. Dielectric reflecting elements may be made of at least two transparent materials, one with a low and the other with a high refractive index. The mirrors are made by creating an alternating stack of these materials, each layer being a quarter wave plate. They can be sputter deposited or evaporated, and are made in the same manner as antireflective coatings on lenses, except that the stacks are structured to reflect, not transmit. Further description of such reflecting elements may be found in D. L. Perry, Applied Optics, vol. 4, (1965), 987. Metallic reflecting elements described herein may be formed on the plates by conventional lithographic processes such as sputtering followed by, for example, electroplating and etching.

In the example shown in FIG. 3A, the top plate 10A and bottom plate 10B are preferably made of electrically non-conducting material such as silica based glasses, silicon dioxide, quartz and polymers. If a polymer is used, it should be chosen so that it does not substantially react with the reflecting elements, solvent or reagents. A preferred material is 0211 glass available from Corning of Corning, N.Y., which is preferred since it comes in desirable 75 $\mu$m thickness. The material to be used for the plates 10A and 10B should be selected to be transparent to the measuring radiation to be used. Electrically non-conducting material of the top plate 10A is disposed between the reflecting element 14A and the channel C. In the example shown, the entirety of plate 14A is disposed between the reflecting element 14A and the channel C. In addition, electrically non-conducting material of the bottom plate 10B is disposed between the reflecting element 14B and the channel C. Apertures 18A and 18B are formed in the reflecting elements 14A and 14B respectively at the waveguide input end 16A and waveguide output end 16B as shown in FIGS. 2 and 5.

The manner of making the absorbance cell of FIG. 3A is as follows. First, bottom plate 10B, which is preferably at least about 200 $\mu$m thick, is microfabricated, as by etching, to form channel C and the associated reservoirs. Holes (not shown in FIG. 1) are drilled to allow access for solutions (see description below in relation to FIGS. 6A and 6B). Second, reflecting element 14B is formed on the surface of the bottom plate 10B opposed to the channel C in the conventional manner described. Preferably, where a fluid injection cell is formed in one part of a chip and the absorbance cell is formed in another part, only the part of the chip which is to form the absorbance cell will be treated by deposition of metal for formation of reflecting elements. Third, top plate 10A is cleaned and then bonded to bottom plate 10B, preferably by heat treating in the case when glass is used for the plates. Fourth, reflecting element 14A is formed on top plate 10A by conventional methods. Apertures 18A and 18B can be formed in the reflecting elements 14A and 14B respectively by etching. At the time that top plate 10A is being manipulated to form the reflecting element 14A and aperture 18A it is bound to bottom plate 10B and therefore may be much thinner than the bottom plate 10B, for example 75 $\mu$m. Top plate 10A may be made even thinner by etching or grinding and polishing the exposed surface after the top plate 10A is bound to bottom plate 10B. A top plate 10A as thin as 30 $\mu$m may be made in this manner before reflecting element 14A is formed on the top plate 10A. Similarly, formation of reflecting element 14B on bottom plate 10B can be delayed until after top plate 10A is bound to bottom plate 10B. Before the reflecting element 14B is formed, bottom plate 10B may be etched (or ground and polished) to make it as thin as may practicably be subsequently manipulated. The minimum thickness for handling and working the plates by processes such as etching is about 150 $\mu$m.

Alternatively, a channel may first be formed in a 200 $\mu$m thick bottom plate 20B, then a 75 $\mu$m top plate 20A bonded to the bottom plate 20B. Next, the bottom plate 20B may be etched (or ground and polished) to a thickness of 75 $\mu$m, leaving the total device 150 $\mu$m thick. Finally, the reflecting elements 24A and 24B may be formed on the top plate 20A and bottom plate 20B respectively.

By the arrangement shown in FIG. 3A, measuring radiation enters the waveguide through the top plate 10A and exits the waveguide through the bottom plate 10B on the opposite side of the device. This arrangement assists in isolating a detector at the waveguide output end from being contaminated with radiation from a radiation source at the waveguide input end.

This arrangement of FIG. 3A suffers from the disadvantage that radiation passing through the waveguide passes through material of the bottom plate required only for the purpose of making the substrate 10 thick enough for material processing. The arrangement of FIG. 3B permits the amount of material of the substrate 10 through which measuring radiation passes to be minimized.

Figure 3B:
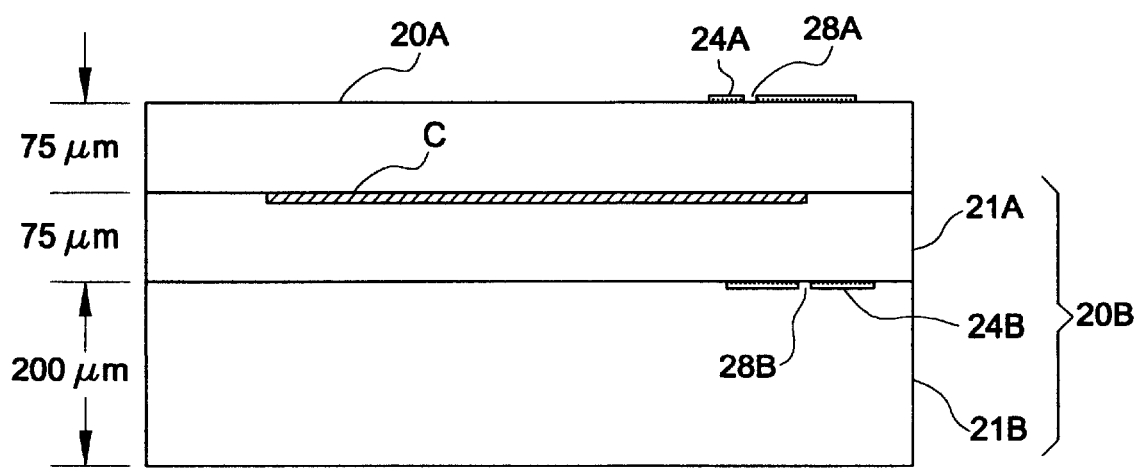
FIG. 3B is a cross-section through a second device according to the invention.

In the absorbance cell of FIG. 3B, bottom plate 20B is formed of two plate segments 21A and 21B. The design of the absorbance cell of FIG. 3B can be understood by the manner in which it is constructed. First, bottom plate segment 21B has reflecting element 24B formed on it in the same manner as reflecting element 14B is formed on plate 10B. An aperture 28B is formed in the reflecting element 24B in the position illustrated in FIG. 5. Second, bottom plate segment 21A is cleaned and bound to bottom plate segment 21B by heat treating, so that bottom plate segment 21A flexes over the top of the reflecting element 24B. Third, channel C and associated reservoirs are formed in bottom plate segment 21A by etching or other micromachining processes. Preferably, bottom plate segment 21B will be at least 200 μm thick or such other thickness that allows subsequent processing without breakage. Bottom plate segment 21A need only be as thick as is required to permit it to be bound without breakage to bottom plate segment 21B. It may initially be 75 μm thick, and then etched (or ground and polished) to a thickness of as little as 20 μm before channel C is formed in it. Fourth, top plate 20A is cleaned and bonded to bottom plate segment 21A by conventional process. Optionally, at this point, top plate 20A may be etched (or ground and polished) as thinly as is feasible, for example to a thickness in the order of 30 μm. Fifth, reflecting element 24A is formed on top plate 20A for example by sputtering followed by electroplating. An aperture 28A is then formed in the reflecting element 24A in the position shown in FIGS. 3B and 5. The result is a three dimensional substrate in which both reflecting elements 24A and 24B are separated from the channel C by electrically non-conducting material, yet the amount of material is kept very low. In an alternative method of making the device of FIG. 3B, the reflecting element 24B is recessed into lower bottom plate segment 21B, and optionally coated and polished so that the top surface of lower bottom plate segment 21B is smooth and flat. In this design, the plate segments 21A and 21B need not be heat bonded, but may be cold bonded without leaving gaps at the edges of the reflecting element 24B. In another method, material of the bottom plate segment 21B may be etched away for deposition of the reflecting element 24B.

In the case when aluminum is used for the reflecting elements, conventional sulphuric acid and hydrogen peroxide mixtures cannot be used. Preferably, for cleaning plates with aluminum elements, a degreasing reagent should be used followed by an acid that does not react with the aluminum of the reflecting element. A preferred degreasing reagent is acetone followed by methanol to remove residue left by the acetone. A preferred acid is nitric acid. It is preferred that the cleaning of the faces to be bonded be followed by a high pressure rinse (for example using a model 2066 high pressure cleaning station available from MicroAutomation, Fermont, Calif., USA, under a class 100 clean hood.

The preferred temperature range of 400–500° C. for heat treating of glass substrate used to form the embodiment of FIG. 3B is selected so that the substrate material has a linear shrinkage in this range. If higher temperature range is used, where there is a non-linear shrinkage, the plates in the three plate embodiment may shrink differentially, which itself makes alignment of features difficult and even curl and fracture. If a lower temperature is used, bonding may not be as effective. Therefore it is preferred to heat treat the plates at a temperature just below the glass softening temperature where the glass has linear shrinkage with time.

While the designs of FIGS. 3A and 3B have their advantages, particularly for use in electrophoresis or other analytical techniques using high voltages, some of the advantages of these designs may be used with a design in which the reflecting elements form part of the borders of the channel C. Two such designs are shown in FIGS. 3C–3E.

In both designs, a bottom plate 30B having a thickness in the order of 200 μm has a channel C formed within a channel bearing surface 32B by conventional techniques. A reflecting element 34B is formed in one portion of the channel C, with an aperture 38B formed in it as for example by etching. The reflecting element 34B extends across a flat portion of the channel C as shown in FIG. 3E. If the reflecting element 34B is metallic and it is desired to prevent it from coming in contact with buffer solution in the channel C, then an electrically insulating layer 33 made for example from the same material as the bottom plate 30B may be formed over the reflecting element 34B. The layer 33 may be made by chemical vapor deposition. Without the insulating layer, or if holes appear in an insulating layer, voltage between the ends of a metal reflecting element within the channel may cause hydrolysis of the buffer solution and ruin the electrophoresis process. If the device incorporates a metallic reflecting element in the channel which is covered with insulation, then since heat bonding may delaminate the reflecting element, other methods of bonding should be used.

Figure 3C:
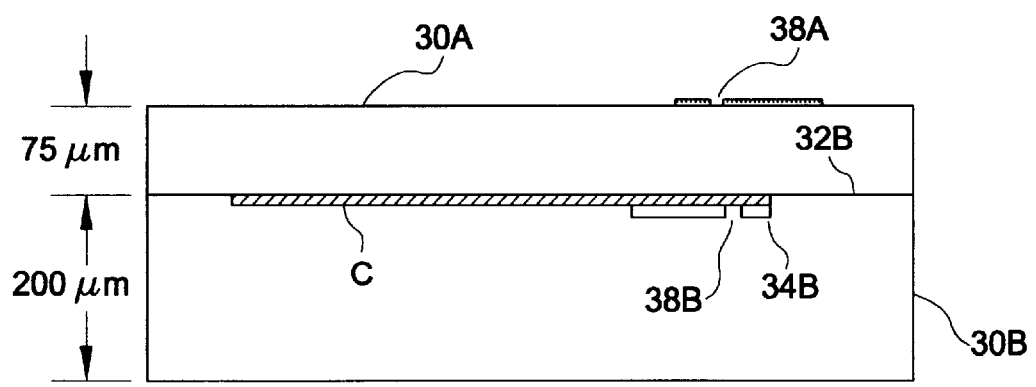
FIG. 3C is a cross-section through a third device according to the invention.

In the example of FIG. 3C, the top plate 30A is bonded to the channel bearing surface 32B of bottom plate 30B. The top plate 30A may be 75 μm thick, and may be etched (or ground and polished) to create a thinner layer before a reflecting element is added to it. Then, a reflecting element 34A is formed on the surface of the top plate 30A in a position to form a waveguide in association with the reflecting element 34B. An aperture 38A is formed in the reflecting element 34A. The device of FIG. 3C is relatively easy to make, yet reduces radiation losses in the material of the plates.

The device of FIG. 3D has the same channel configuration as the device of FIG. 3C as shown in FIG. 3E, but further minimizes propagation losses by having a reflecting element 44A formed in the channel facing surface 42A of top plate 40A. Bottom plate 40B is formed in the same manner as bottom plate 30B, with reflecting element 44B and aperture 48B. Top plate 40A is initially about 200 μm thick and has a reflecting element 44A formed in one of its surfaces, which becomes the channel facing surface 42A. Reflecting element 44A preferably extends laterally well beyond the channel C as shown in FIG. 3E similar to the top plate 10A shown in FIG. 1, to help prevent radiation reflecting from the reflecting element 40B escaping from the waveguide. Top plate 40A is then cold bonded or clamped to the bottom plate 40B and etched (or ground and polished) to a suitable thickness, for example 40 μm. The reflecting element 44A may also be coated with an electrically insulating material before top plate 40A is bonded to bottom plate 40B.

Figure 4:
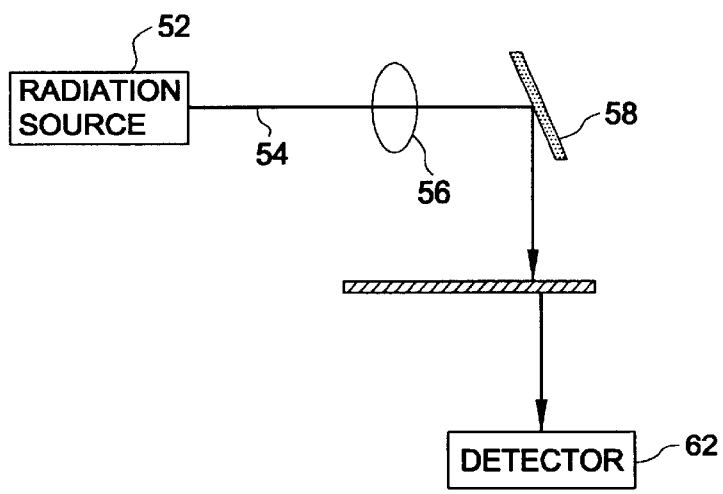
FIG. 4 shows a measuring radiation source and radiation detection system for use as part of an embodiment of the invention.

As shown in FIG. 5, the input apertures 18A, 28A, 38A and 48A are used for introduction of measuring radiation into the waveguide, and the output apertures 18B, 28B, 38B and 48B are used for egress of measuring radiation from the waveguide. The radiation delivery system is shown in FIG. 4. A source of measuring radiation, which typically is visible or UV light, as for example, a 2 mW helium-neon laser 52 directs a beam of radiation 54 through a focusing lens 56 to a tiltable mirror 58 mounted on a rotary stage (not shown, but may be for example a model 481-A rotary stage available from Newport, Mississauga, ON, Canada). A white light source may be used with a wavelength selection device, or a UV source such as a mercury lamp may also be used. The mirror 58 may be oriented using the rotary stage to direct the measuring radiation towards an input aperture in the waveguide at a pre-selected angle $\alpha$ to a normal N to the reflecting surfaces of the waveguide.

As seen in the results described in relation to the graphs in this patent document, the selection of the input angle changes the number of reflections of the measuring radiation in the waveguide. The measuring radiation thus introduced into the waveguide through the material of the top plate propagates at an angle $\alpha$ to a normal to the reflecting surfaces as the radiation passes through the top plate. For the purpose of ease of alignment of the direction of propagation of the measuring radiation into the waveguide, it is believed to be important that the radiation have a free space mode of propagation as it enters the waveguide, since then the angle of incidence of the radiation as it enters the waveguide may be controlled by an orientable mirror 58. The lens 56 should focus the radiation to a focal spot at the input aperture that is approximately the same size as the input aperture, as for example about 30 $\mu$m diameter.

Detection of light or other radiation emerging from the output aperture of the waveguide is obtained by placing a photodiode or equivalent detector 62 (FIG. 4) in a position such that it intercepts radiation emerging from the output aperture 18B, 28B, 38B or 48B. Various conventional photodiodes may be used such as those available from Melles Griot. In the case of the embodiment of FIG. 3A, the photodiode 62 may be placed directly over the reflecting element 14B, but otherwise is placed closely adjacent the bottom plate 20B, 30B and 40B. Lenses may be used to focus the emerging radiation onto the photodiode 62 as required. Buffer and sample are supplied by conventional pumps and supply lines. Fluid supply may be computer controlled using techniques known in the art, and analysis of the detected radiation may be carried out with a computer using software such as Labview™ software available from National Instruments Corp. Austin, Tex.). Conventional electrodes, voltage source, and other conventional apparatus should be used for the establishment of electrophoretic voltage through the sample and buffer to drive the electrophoresis process.

The detection zone (distance between input and output apertures) should not be more than about 300 $\mu$m long and is preferably about 200 $\mu$m long with a 15–25 $\mu$m depth of channel. For manufacturing, alignment markings on the plates should be used to ensure accurate placement of the reflecting elements 14A, 24A, 34A, 44A and 14B, 24B in relation to the channel C.

The channel C may also be formed partly in the top plate, but this device is harder to align. The top plate and bottom plate should have matching thermal expansion properties when they may be subject to raised processing temperatures. The aperture size should be about the same width as the channel, about 20 $\mu$m to 100 $\mu$m width.

The number of reflections made by the radiation from the reflecting surfaces as the measuring radiation propagates along the waveguide from input aperture to output aperture is a function of the distance D between the plates, the distance L between the centers of the apertures and the angle $\alpha$ between the direction of propagation of the measuring radiation into the waveguide at the aperture and a normal to the reflecting surfaces. In general, the greater the number of reflections the greater the sensitivity of the device. However, the signal to noise ratio in the detected signal varies with number of reflections for a given reflectivity, R, of the reflecting elements in a manner known for waveguides formed between partially reflecting surfaces, as discussed in for example Werle et al, "Signal to Noise Ratio Analysis in Laser Absorption Spectrometers using Optical Multipass Cell", Applied Optics vol. 30, no. 4, February 1991. The signal to noise ratio reaches a peak at a certain number of reflections and decreases when the number of reflections is above or below this peak. Combining the effect of the reflectivity of the reflecting surfaces and the increasing sensitivity with increasing number of reflections, for a reflecting surface with a reflectivity of about 95%, the optimum number of reflections is between about 10 and 30. Given an optimum number of reflections, which may be determined empirically for a given laser and reflecting elements, the angle of incidence of the incident radiation and geometry of the waveguide may be determined. Some examples are shown in the following table, where D is the total thickness in microns of the top and bottom plates, N is the number of reflections, L is the distance between the centers of the apertures in microns and $\alpha$ is the angle of incidence in degrees of the measuring radiation as it enters the waveguide. The channel thickness is assumed to be about 30 $\mu$m, but it is not a significant factor and has been left out of the figures for D. The reflectivity of the reflecting elements is 95% in each case.

| D | L | N | $\alpha$ |
|---|---|---|---|
| 275 | 200 | 20 | 3.1 |
| 275 | 200 | 10 | 6.2 |
| 150 | 200 | 20 | 5.7 |
| 150 | 200 | 40 | 3.8 |
| 70 | 200 | 24 | 10 |
| 70 | 200 | 40 | 6 |
| 70 | 200 | 20 | 11.8 |
| 70 | 50 | 20 | 3 |
| 40 | 30 | 20 | 3 |
| 75 | 200 | 20 | 11 |

Separation of proteins may be enhanced by coating the interior of the channel C with polysiloxane. A solution of polydimethylsiloxane is injected into the channel C and the substrate is then placed in an oven and baked at 200–500° C. (400° C. being preferable) for at least 30 min., with 1 hour being preferable. The solvent in the solution can be any volatile solvent able to dissolve the polymer, and the concentration of solvent should be in a suitable range that the solution is not too viscous to inject into the capillary, for example in the range from 0.1% to 50% with 1% seeming preferable. Application of one coating will work, but two platings is optimal. The solution may be left in the channel before heating, but it is preferably vacuumed or blown out. A neutral or charged surfactant, such as commercially available neutral Tween 20™ and Brij 35™, or charged dodecyl-sulphate or cetyltrimethylammonium, at concentrations from 0.001 to 1 wt %, should be added to the buffer being used for separation. Polysiloxane may also be used to coat a reflecting element deposited in a channel, providing cold or cool bonding techniques are used for the manufacture of the device.

Figure 6A:
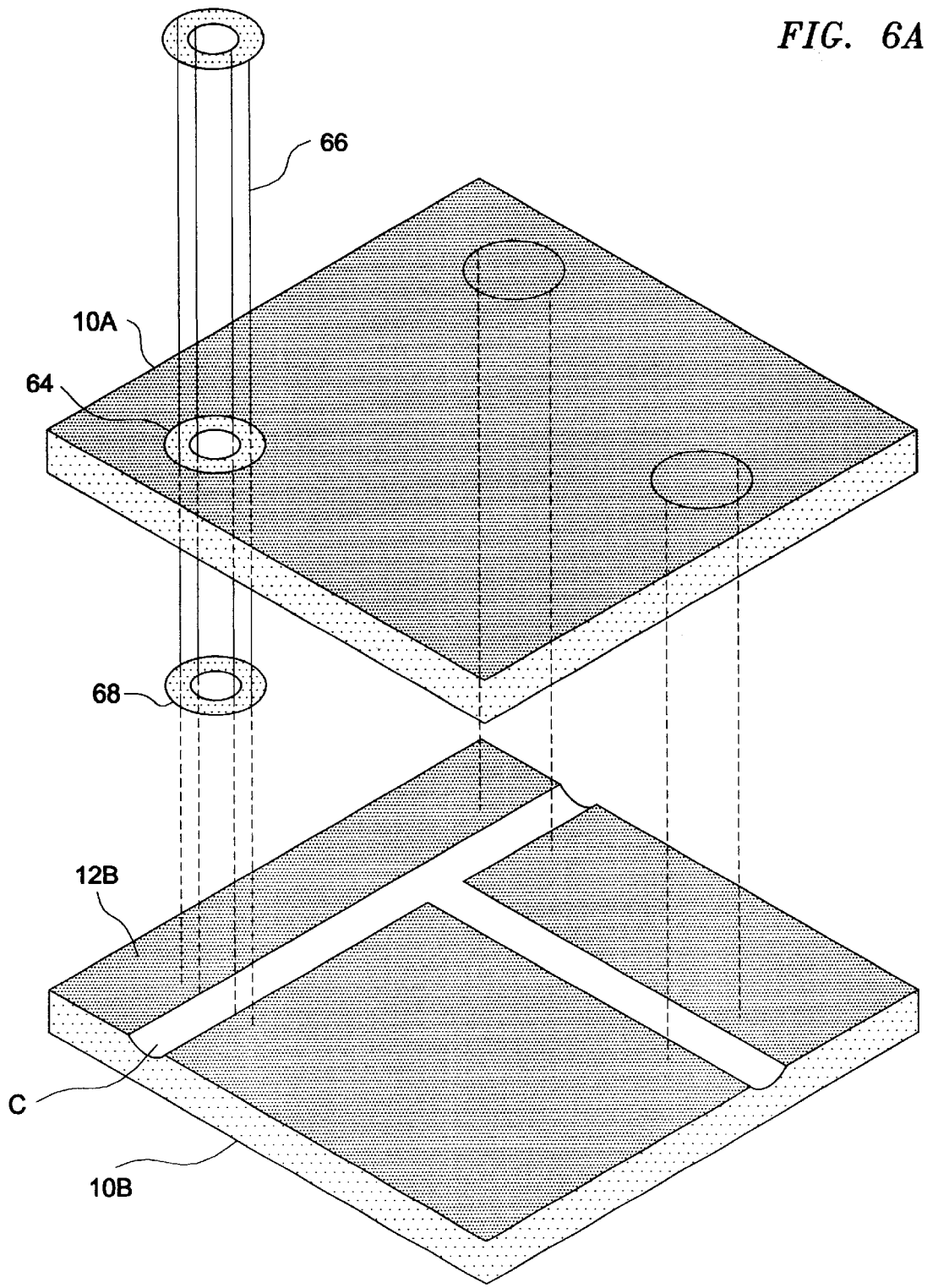
FIG. 6A is a perspective, exploded view, of a low dead volume connector for use in the invention.

For input of solution into channels formed in the substrate 10, it is desirable to have low or no dead volume in the connection. A preferred connector is shown in FIG. 6A. A hole 64 is formed in the top plate 10A as by drilling with a 1.9 mm diameter diamond drill bit. A capillary 66 with a polished flat end 68 at 90° to the axis of the capillary, and having a diameter equal to the diameter of the hole 64, is inserted into the hole 64 until it butts up, centered over the channel, against the channel bearing surface 12B of the bottom plate 10B. The capillary 66 may then be clamped or glued in place. The capillary 66 thus provides a low dead volume connector for fluids entering the channel C.

The two plate design of a capillary to chip coupling shown in FIG. 6A may suffer from poor sealing of the flat end 68 of the fiber to the substrate, and to a poor fit between the capillary outside diameter and the diameter of the hole in the plate. As an example of a possible problem, glue used to seal the capillary in place may leak down the outside edge of the capillary and into the flow channel C. While these problems may be overcome with careful manufacturing, an alternative that is easier to manufacture is described here.

Figure 6B:
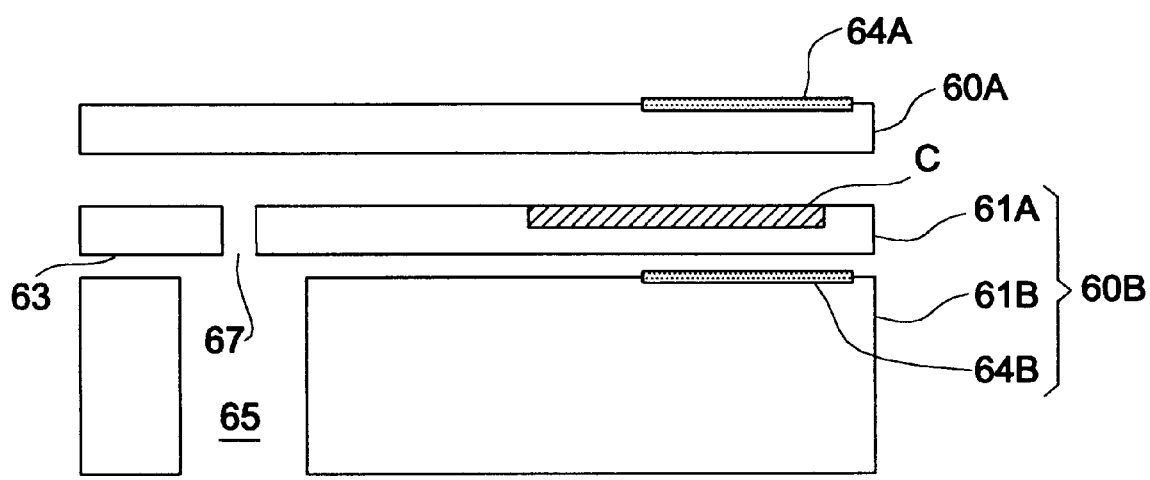
FIG. 6B is a perspective, exploded view, of a second embodiment of a low dead volume connector for use in the invention.

Use of a three plate design as shown in FIG. 6B alleviates these problems significantly, by allowing the central plate to serve in the capacity of a washer. In this design a bottom plate segment 61B has a hole 65 drilled in it to a diameter to allow access of a capillary over top of the flow channel C etched in one of the other plates shown here as top plate segment 61A.

The top plate segment 61A is made of thin glass (75 μm or less) and has a hole 67 of 200 μm or lower diameter formed in it by laser ablation, photolithography and etching, or ultrasonic drilling. A preferred embodiment is for the hole 67 to be formed by etching to a diameter of 75 to 150 μm. Another preferred embodiment is for the hole 67 diameter to match the etch channel C dimensions, requiring formation by laser ablation with the methods known for ablation of quartz.

The above design can be incorporated into the three layer absorbance cell design of FIG. 3B in the following manner. Bottom plate segment 61B has a reflecting element 64B deposited and patterned, and aligned through holes are drilled for access to the channel C and other channels etched in the plate. A 75 μm top plate segment 61A is bonded to bottom plate segment 61B by any of the methods described above in relation to FIG. 3B. The through holes may be etched or formed in top plate segment 61A, and then the indented flow channel C and other flow channels may be patterned and etched. Use of photolithographic methods facilitates alignment of the through holes with the flow channels and aperture in the reflecting elements. A top plate 60A is then bonded to top plate segment 61A and a reflecting element 64A formed on the top plate 60A by photolithographic methods. A capillary (not shown, but may be the same as capillary 66 in FIG. 6A) may then be inserted through hole 65 until it butts up against the top plate segment 61A. The capillary should be selected so that its interior diameter is the same as the outer diameter of the hole 67 and the outer diameter of the capillary should be the same as the diameter of hole 65. The capillary should be centered over the hole 67. The hole 67 may be considered a channel passing through the top plate segment 61A. The face 63 of the top plate segment 61A should be flat, or at least have a surface contour around the hole 67 that matches the shape of the end of the capillary.

Propagation Characteristics of the Radiation

Figure 7:
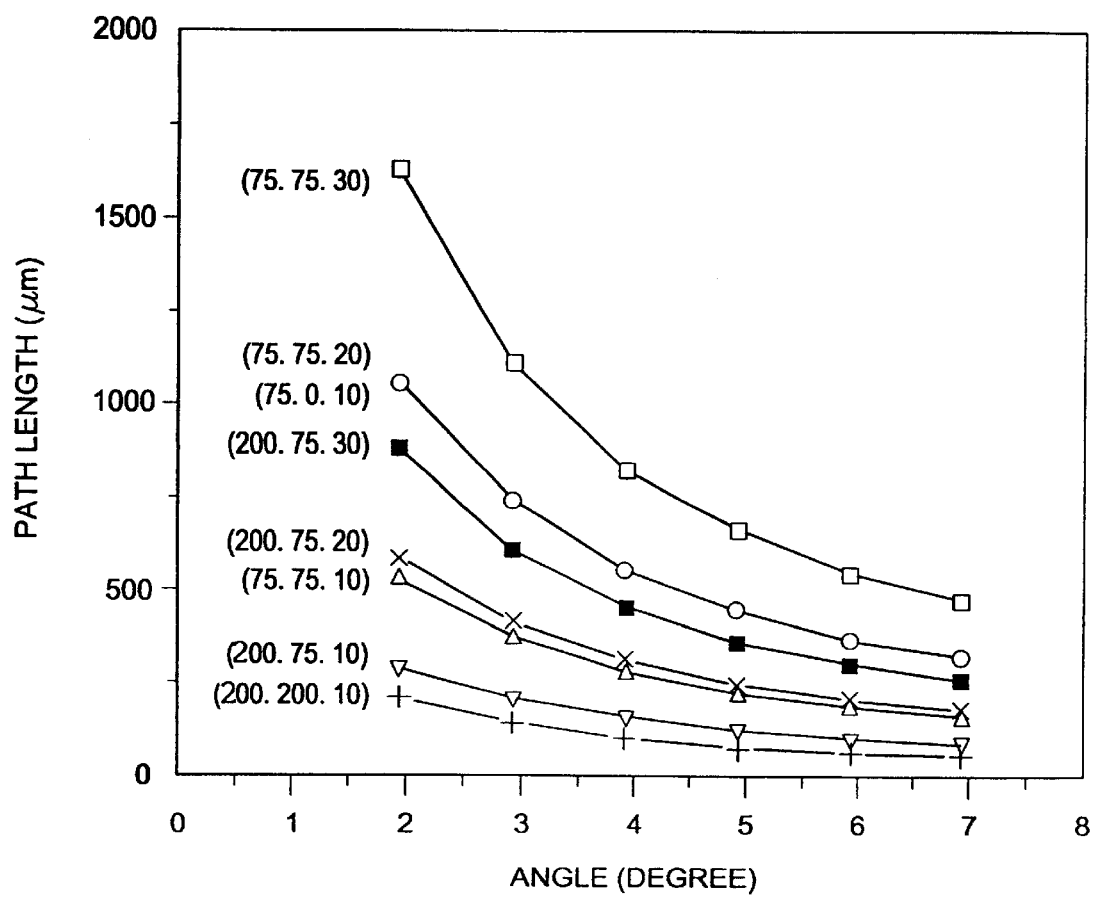
FIG. 7 is a graph showing calculated variation of path length of a waveguide with various dimensions of plate thickness and channel depth.
Figure 8:
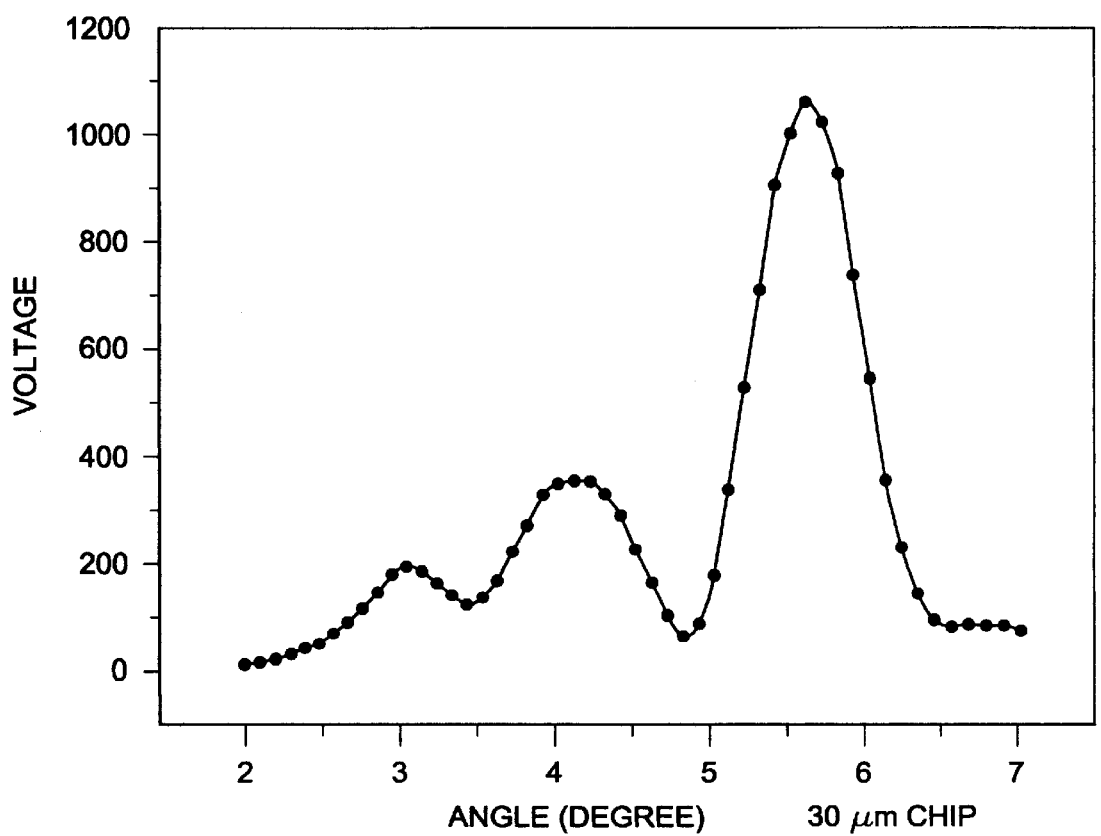
FIG. 8 is a graph showing recorded variation of intensity (as represented by measured voltage) as angle of incidence varies for a chip with 30 Am depth of channel.

Calculated path length of the radiation through the channel C is a function of the thickness of the plates (a, b in the triplet (a, b, c) in FIG. 7), channel depth (c), and angle of incidence (x axis) of the radiation into the waveguide. Path length increases as plate thickness decreases, channel depth increases and angle of incidence decreases. However, in practice, measured variation of path length, by comparison with calibrated intensities, is somewhat lower than calculated, possibly due to surface roughness, reflection of light on the side walls and bending of the top plate during a thermal bonding step. Variation of intensity of radiation received at the photodiode 62 with angle of incidence of the radiation into the waveguide is shown in FIG. 8. The maxima are believed to indicate when the last reflection point in the waveguide coincides with the output aperture. The device should be operated at one of the maxima. Since the reflecting elements are lossy, too many reflections results in excessive losses of radiation. If the angle of incidence is too low, then there are too many reflections. Thus, it is preferred to operate the device with an angle of incidence greater than about 2° (with aluminum mirrors). On the other hand, the number of reflections decreases with increasing angle of incidence and it is desirable that the angle of incidence be lower than about 12° for a device with reflectivity of the reflecting elements about 95% and for which the plate thickness D is between about 40 μm and 275 μm and the aperture spacing L is about 30 μm to 200 μm. It is desirable that there be at least 4 reflections and fewer than 40 for a moderately reflective reflecting element. The resulting effective path length may be made longer than the length of the waveguide.

In general the aperture spacing L should not be less than the aperture diameter, and for an aperture of about 30 μm, the spacing L should be not less than 60 μm.

Figure 9:
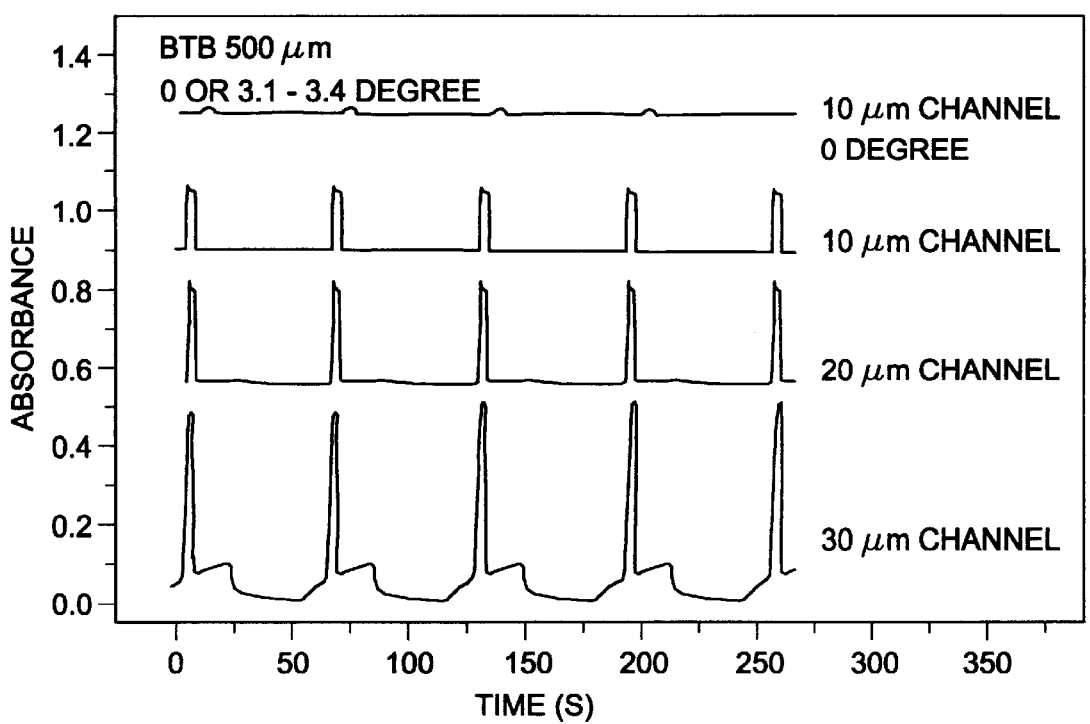
FIG. 9 is a graph showing separation efficiency of a device according to the invention with varying channel depth.

Separation results using the device of FIG. 3B are shown in FIG. 9 using $5 \times 10^{-4}$ M bromothymol blue (BTB) and a 5 mM phosphate buffer, pH=10.5. Angle of incidence is 0° for the top trace, 3.1° for the second trace, 3.4° for the third trace, and 3.1 for the fourth trace. Channel depth is 10 μm (top trace), 10 μm 20 μm and 30 μm (bottom trace). As can be seen in FIG. 9, increased sensitivity due to increased path length is partially offset for deeper channels by increased base line, most likely due to the Joule heating effect, which causes an increase in the temperature and thus refractive index of the buffer solution. Study of the disclosed device of FIG. 3B shows that decrease of separation efficiency occurs with increased concentration of BTB, most likely due to adsorption of BTB on the channel wall. This effect may be alleviated with use of polysiloxane coating on the channel wall.

A person skilled in the art could make immaterial modifications to the invention described in this patent document without departing from the essence of the invention that is intended to be covered by the scope of the claims that follow.

The embodiments of the invention in which an exclusive property or privilege is claimed are defined as follows:

1. An absorbance cell for a microfluid device, the absorbance cell comprising:
    a bottom plate having a channel bearing surface in which a channel is defined, the channel having a fluid inlet and fluid outlet, the channel having a depth of about 10–30 μm;
    a top plate having a channel facing surface bound to the channel bearing surface of the bottom plate;
    first and second reflecting elements formed on opposed sides of the channel to form a waveguide through which the channel extends such that radiation propagating along the waveguide makes multiple passes across the channel, the waveguide having a radiation input end and a radiation output end; and electrically non-conducting material of one of the top plate and bottom plate being disposed between the first reflecting element and the channel, the electrically non-conducting material being transparent to measuring radiation.

2. The absorbance cell of claim 1 in which electrically non-conducting material of the top plate is disposed between the first reflecting element and the channel.

3. The absorbance cell of claim 2 in which electrically non-conducting material of the bottom plate is disposed between the second reflecting element and the channel, the electrically non-conducting material of the bottom plate being transparent to measuring radiation.

4. The absorbance cell of claim 1 in which the waveguide input end and the waveguide output end are arranged so that measuring radiation enters the waveguide through one of the top plate and the bottom plate and exits the waveguide through the other of the top plate and the bottom plate.

5. The absorbance cell of claim 1 in which the first reflecting element is formed on a first face of a first plate segment, the first face of the first plate segment abuts against a second face of a second plate segment, and together the first and second plate segments form the bottom plate.

6. The absorbance cell of claim 5 in which the fluid inlet comprises:

a flat ended capillary inserted through a first hole in the second plate segment, the flat ended capillary and the first hole each having a diameter and the flat ended capillary being butted up against a flat surface of the first plate segment in which a second hole is defined, the second hole being in fluid communication with the channel, the channel having a depth, a width and a length longer than the width, the second hole being centered over the width of the channel and the flat ended capillary being centered over the second hole.

7. The absorbance cell of claim 6 in which the first hole and the capillary have equal diameter.

8. The absorbance cell of claim 1 in which the waveguide input end is arranged such that radiation introduced into the waveguide through one of the top plate and bottom plate propagates at an angle $\alpha > 0°$ to a normal to the reflecting surfaces as the radiation passes through the one of the top plate and bottom plate.

9. The absorbance cell of claim 8 in which the angle $\alpha$ is selected so that the number of reflections of radiation propagating along the waveguide is from the range 10 to 30.

10. The absorbance cell of claim 8 in which the angle $\alpha$ is greater than 2°.

11. The absorbance cell of claim 1 in which the angle $\alpha$ is selected so that the number of reflections of radiation propagating along the waveguide is greater than 4.

12. The absorbance cell of claim 1 in which the waveguide input end is arranged such that radiation introduced to the waveguide has a free space mode of propagation.

13. The absorbance cell of claim 1 further comprising a measuring radiation source and a measuring radiation detector, the measuring radiation detector having a detection region, and in which the reflecting elements extend laterally to cover the detection region and form a shield between the measuring radiation source and the measuring radiation detector.

14. The absorbance cell of claim 1 further comprising an input aperture in one of the first and second reflecting elements for introduction of measuring radiation into the waveguide, and an output aperture in the other of the first and second reflecting elements for egress of measuring radiation from the waveguide.

15. The absorbance cell of claim 1 in which the fluid inlet comprises:

a flat ended capillary inserted through a hole in the top plate, with the flat ended capillary butting up against the channel bearing surface of the bottom plate, the channel having a depth, width and length longer than the width and with the flat ended capillary centered over the width of the channel.

16. The absorbance cell of claim 1 in which the channel has a depth from 15 to 25 $\mu$m.

17. An absorbance cell for a microfluid device, the absorbance cell comprising:

a bottom plate having a channel bearing surface in which a channel is defined, the channel having a fluid inlet and fluid outlet, the channel having a depth of about 10–30 $\mu$m;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end; and the waveguide input end and the waveguide output end being arranged so that radiation enters the waveguide through one of the top plate and the bottom plate and exits the waveguide through the other of the top plate and the bottom plate.

18. An absorbance cell for a microfluid device, the absorbance cell comprising:

a bottom plate having a channel bearing surface in which a channel is defined, the channel having a fluid inlet and fluid outlet, the channel having a depth of about 10–30 $\mu$m;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end; and an input aperture in one of the first and second reflecting elements for introduction of measuring radiation into the waveguide, and an output aperture in the other of the first and second reflecting elements for egress of measuring radiation from the waveguide.

19. An absorbance cell for a microfluid device, the absorbance cell comprising:

a bottom plate having a channel bearing surface in which a channel is defined, the channel having a fluid inlet and fluid outlet, the channel having a depth of about 10–30 $\mu$m;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end; and the waveguide input end being arranged such that radiation introduced into the waveguide through one of the top plate and bottom plate propagates at an angle α to a normal to the reflecting surfaces as the radiation passes through the one of the top plate and bottom plate.

20. The absorbance cell of claim 19 in which the angle α is selected so that the number of reflections of radiation propagating along the waveguide is from the range 10 to 30.

21. The absorbance cell of claim 19 in which the angle α is greater than 2°.

22. The absorbance cell of claim 19 in which the angle α is selected so that the number of reflections of radiation propagating along the waveguide is greater than 4.

23. An absorbance cell for a microfluid device, the absorbance cell comprising:
   a bottom plate having a channel bearing surface in which a channel is defined, the channel having a fluid inlet and fluid outlet the channel having a depth of about 10–30 μm;
   a top plate having a channel facing surface bound to the channel bearing surface of the bottom plate;
   first and second reflecting elements formed on opposed sides of the channel to form a waveguide through which the channel extends such that radiation propagating along the waveguide makes multiple passes across the channel, the waveguide having a radiation input end and a radiation output end; and
   the waveguide input end being arranged such that radiation introduced to the waveguide has a free space mode of propagation.

24. An absorbance cell for a microfluid device, the absorbance cell comprising:
   a bottom plate having a channel bearing surface in which a channel is defined, the channel having a fluid inlet and fluid outlet the channel having a depth of about 10–30 μm;
   a top plate having a channel facing surface bound to the channel bearing surface of the bottom plate;
   first and second reflecting elements formed on opposed sides of the channel to form a waveguide through which the channel extends such that radiation propagating along the waveguide makes multiple passes across the channel, the waveguide having a radiation input end and a radiation output end; and
   the reflecting elements extending laterally to form a shield between a measuring radiation source and a measuring radiation detector.

25. An absorbance cell for a microfluid device, the absorbance cell comprising:
   a bottom plate having a channel bearing surface in which a channel is defined, the channel having a fluid inlet and fluid outlet the channel having a depth of about 10–30 μm;
   a top plate having a channel facing surface bound to the channel bearing surface of the bottom plate;
   first and second reflecting elements formed on opposed sides of the channel to form a waveguide through which the channel extends such that radiation propagating along the waveguide makes multiple passes across the channel, the waveguide having a radiation input end and a radiation output end; and
   electrically non-conducting material being disposed between the first and second reflecting elements and the channel, the electrically non-conducting material being transparent to measuring radiation.

26. The absorbance cell of claim 25 in which the electrically non-conducting material is made of the same material as the top and bottom plates.

27. The absorbance cell of claim 25 in which the waveguide input end and the waveguide output end are arranged so that measuring radiation enters the waveguide through one of the top plate and the bottom plate and exits the waveguide through the other of the top plate and the bottom plate.

28. The absorbance cell of claim 27 in which the first reflecting element is formed on a first face of a first plate segment, the first face of the first plate segment abuts against a second face of a second plate segment, and together the first and second plate segments form the bottom plate.

29. The absorbance cell of claim 28 in which the fluid inlet comprises:
   a flat ended capillary inserted through a hole in the second plate segment and butted up against a flat surface of the first plate segment in which a hole is defined, the hole being in fluid communication with the channel, the channel having a depth, a width and a length longer than the width, and the flat ended capillary being centered over the width of the channel.

30. The absorbence cell of claim 28 in which the absorbence cell has been made by the steps of:
   forming the first reflecting element on the first plate segment;
   bonding the second plate segment to the first plate segment by heat treating the first and second plate segments with the first reflecting element disposed between the first and second plate segments;
   forming the channel in the second plate segment;
   bonding the top plate to the second plate segment; and
   forming the second reflecting element on the top plate.

31. The absorbance cell of claim 25 further comprising an input aperture in one of the first and second reflecting elements for introduction of measuring radiation into the waveguide, and an output aperture in the other of the first and second reflecting elements for egress of measuring radiation from the waveguide.

32. The absorbance cell of claim 25 in which the waveguide input end is arranged such that radiation introduced into the waveguide through one of the top plate and bottom plate propagates at an angle α>0° to a normal to the reflecting surfaces as the radiation passes through the one of the top plate and bottom plate.

33. The absorbance cell of claim 32 in which the angle α is selected so that the number of reflections of radiation propagating along the waveguide is from the range 10 to 30.

34. The absorbance cell of claim 32 in which the angle α is greater than 2°.

35. The absorbance cell of claim 32 in which the angle α is selected so that the number of reflections of radiation propagating along the waveguide is greater than 4.

36. The absorbance cell of claim 25 in which the waveguide input end is arranged such that radiation introduced to the waveguide has a free space mode of propagation.

37. The absorbance cell of claim 25 in which the reflecting elements extend laterally to form a shield between a measuring radiation source and a measuring radiation detector.

38. The absorbance cell of claim 25 further comprising:
   a detector of radiation exiting the radiation output end, the detector having a detection region; and
   at least one of the reflecting elements extending laterally to cover the detection region of the detector.

39. The absorbance cell of claim 38 in which the at least one of the reflecting elements extends laterally more than a millimeter.

40. The absorbence cell of claim 38 in which the reflecting elements are square.

41. The absorbance cell of claim 25 in which the channel is coated with polysiloxane.

42. The absorbance cell of claim 25 in which the fluid inlet comprises:

a flat ended capillary inserted through a hole in the top plate, with the flat ended capillary butting up against the channel bearing surface of the bottom plate, the channel having a depth, width and length longer than the width, and with the flat ended capillary centered over the width of the channel.

43. The absorbance cell of claim 25 in which the channel has a depth from 15 to 25 μm.

44. The absorbance cell of claim 25 in which the first reflecting element is formed on the channel bearing surface of the bottom plate.

45. The absorbence cell of claim 44 in which the first reflecting element is coated with the electrically non-conducting material.

46. The absorbence cell of claim 44 in which the second reflecting element is formed on the channel facing surface of the top plate.

47. The absorbence cell of claim 46 in which the second reflecting element is coated with the electrically non-conducting material.

48. An absorbance cell for a microfluid device, the absorbance cell comprising:

a bottom plate having a channel bearing surface in which a channel is defined, the channel having a fluid inlet and fluid outlet;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end;

the first reflecting element being formed on a first face of a first plate segment, the first face of the first plate segment abutting against a second face of a second plate segment, and together the first and second plate segments forming the bottom plate;

electrically non-conducting material of one of the top plate and bottom plate being disposed between the first reflecting element and the channel, the electrically non-conducting material being transparent to measuring radiation; and the fluid inlet comprising a flat ended capillary inserted through a first hole in the second plate segment, the flat ended capillary and the first hole each having a diameter and the flat ended capillary being butted up against a flat surface of the first plate segment in which a second hole is defined, the second hole being in fluid communication with the channel, the channel having a depth, a width and a length longer than the width, the second hole being centered over the width of the channel and the flat ended capillary being centered over the second hole.

49. The absorbance cell of claim 48 in which the first hole and the capillary have equal diameter.

50. An absorbance cell for a microfluid device, the absorbance cell comprising:

a bottom plate having a channel bearing surface in which a channel is defined, the channel having a fluid inlet and fluid outlet;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end;

a flat ended capillary inserted through a hole in the top plate, with the flat ended capillary butting up against the channel bearing surface of the bottom plate, the channel having a depth, width and length longer than the width and with the flat ended capillary centered over the width of the channel; and electrically non-conducting material of one of the top plate and bottom plate being disposed between the first reflecting element and the channel, the electrically non-conducting material being transparent to measuring radiation.

51. An absorbance cell for a microfluid device, the absorbance cell comprising:

a bottom plate having a channel bearing surface in which a channel is defined, the channel having a fluid inlet and fluid outlet;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end;

electrically non-conducting material being disposed between the first and second reflecting elements and the channel, the electrically non-conducting material being transparent to measuring radiation;

the waveguide input end and the waveguide output end being arranged so that measuring radiation enters the waveguide through one of the top plate and the bottom plate and exits the waveguide through the other of the top plate and the bottom plate;

the first reflecting element being formed on a first face of a first plate segment, the first face of the first plate segment abutting against a second face of a second plate segment, and together the first and second plate segments forming the bottom plate; and a flat ended capillary inserted through a hole in the second plate segment and butted up against a flat surface of the first plate segment in which a hole is defined, the hole being in fluid communication with the channel, the channel having a depth, a width and a length longer than the width, and the flat ended capillary being centered over the width of the channel.

52. An absorbance cell for a microfluid device, the absorbance cell comprising:

a bottom plate having a channel bearing surface in which a channel is defined, the channel having a fluid inlet and fluid outlet;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end;

electrically non-conducting material being disposed between the first and second reflecting elements and the channel, the electrically non-conducting material being transparent to measuring radiation; and a flat ended capillary inserted through a hole in the top plate, with the flat ended capillary butting up against the channel bearing surface of the bottom plate, the channel having a depth, width and length longer than the width, and with the flat ended capillary centered over the width of the channel.

53. An absorbance cell for a microfluid device, the absorbance cell comprising:

a bottom plate having a channel bearing surface in which a channel is defined, the channel having a fluid inlet and fluid outlet, the channel having a width and a depth, and the width of the channel being about 20–100 μm;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end; and electrically non-conducting material of one of the top plate and bottom plate being disposed between the first reflecting element and the channel, the electrically non-conducting material being transparent to measuring radiation.

54. The absorbance cell of claim 53 in which electrically non-conducting material of the top plate is disposed between the first reflecting element and the channel.

55. The absorbance cell of claim 54 in which electrically non-conducting material of the bottom plate is disposed between the second reflecting element and the channel, the electrically non-conducting material of the bottom plate being transparent to measuring radiation.

56. The absorbance cell of claim 53 in which the waveguide input end and the waveguide output end are arranged so that measuring radiation enters the waveguide through one of the top plate and the bottom plate and exits the waveguide through the other of the top plate and the bottom plate.

57. The absorbance cell of claim 53 in which the first reflecting element is formed on a first face of a first plate segment, the first face of the first plate segment abuts against a second face of a second plate segment, and together the first and second plate segments form the bottom plate.

58. The absorbance cell of claim 57 in which the fluid inlet comprises:

a flat ended capillary inserted through a first hole in the second plate segment, the flat ended capillary and the hole each having a diameter and the flat ended capillary being butted up against a flat surface of the first plate segment in which a second hole is defined, the second hole being in fluid communication with the channel, the channel having a depth, a width and a length longer than the width, the second hole being centered over the width of the channel and the flat ended capillary being centered over the second hole.

59. The absorbance cell of claim 58 in which the first hole and the capillary have equal diameter.

60. The absorbance cell of claim 53 further comprising an input aperture in one of the first and second reflecting elements for introduction of measuring radiation into the waveguide, and an output aperture in the other of the first and second reflecting elements for egress of measuring radiation from the waveguide.

61. The absorbance cell of claim 53 in which the waveguide input end is arranged such that radiation introduced into the waveguide through one of the top plate and bottom plate propagates at an angle $\alpha > 0°$ to a normal to the reflecting surfaces as the radiation passes through the one of the top plate and bottom plate.

62. The absorbance cell of claim 61 in which the angle $\alpha$ is selected so that the number of reflections of radiation propagating along the waveguide is from the range 10 to 30.

63. The absorbance cell of claim 61 in which the angle $\alpha$ is greater than 2°.

64. The absorbance cell of claim 61 in which the angle $\alpha$ is selected so that the number of reflections of radiation propagating along the waveguide is greater than 4.

65. The absorbance cell of claim 53 in which the waveguide input end is arranged such that radiation introduced to the waveguide has a free space mode of propagation.

66. The absorbance cell of claim 53 further comprising a measuring radiation source and a measuring radiation detector, the measuring radiation detector having a detection region, and in which the reflecting elements extend laterally to cover the detection region and form a shield between the measuring radiation source and the measuring radiation detector.

67. The absorbance cell of claim 53 in which the fluid inlet comprises:

a flat ended capillary inserted through a hole in the top plate, with the flat ended capillary butting up against the channel bearing surface of the bottom plate, the channel having a depth, width and length longer than the width and with the flat ended capillary centered over the width of the channel.

68. The absorbance cell of claim 53 in which the channel has a depth from 10 to 30 μm.

69. An absorbance cell for a microfluid device, the absorbance cell comprising:

a bottom plate having a channel bearing surface in which a channel is defined, the channel having a fluid inlet and fluid outlet, the channel having a width and a depth, and the width of the channel being about 20–100 μm;

a top plate having a channel facing surface bound to the channel bearing surface of the bottom plate;

first and second reflecting elements formed on opposed sides of the channel to form a waveguide through which the channel extends such that radiation propagating along the waveguide makes multiple passes across the channel, the waveguide having a radiation input end and a radiation output end; and electrically non-conducting material being disposed between the first and second reflecting elements and the channel, the electrically non-conducting material being transparent to measuring radiation.

70. The absorbance cell of claim 69 in which the electrically non-conducting material is made of the same material as the top and bottom plates.

71. The absorbance cell of claim 69 in which the waveguide input end and the waveguide output end are arranged so that measuring radiation enters the waveguide through one of the top plate and the bottom plate and exits the waveguide through the other of the top plate and the bottom plate.

72. The absorbance cell of claim 71 in which the first reflecting element is formed on a first face of a first plate segment, the first face of the first plate segment abuts against a second face of a second plate segment, and together the first and second plate segments form the bottom plate.

73. The absorbance cell of claim 72 in which the fluid inlet comprises:

a flat ended capillary inserted through a hole in the second plate segment and butted up against a flat surface of the first plate segment in which a hole is defined, the hole being in fluid communication with the channel, the channel having a depth, a width and a length longer than the width, and the flat ended capillary being centered over the width of the channel.

74. The absorbance cell of claim 72 in which the absorbance cell has been made by the steps of:

forming a first reflecting element on the first plate segment;

bonding the second plate segment to the first plate segment by heat treating the first and second plate segments with the first reflecting element disposed between the first and second plate segments;

forming the channel in the second plate segment;

bonding the top plate to the second plate segment; and forming the second reflecting element on the top plate.

75. The absorbance cell of claim 69 further comprising an input aperture in one of the first and second reflecting elements for introduction of measuring radiation into the waveguide, and an output aperture in the other of the first and second reflecting elements for egress of measuring radiation from the waveguide.

76. The absorbance cell of claim 69 in which the waveguide input end is arranged such that radiation introduced into the waveguide through one of the top plate and bottom plate propagates at an angle $\alpha > 0°$ to a normal to the reflecting surfaces as the radiation passes through the one of the top plate and bottom plate.

77. The absorbance cell of claim 76 in which the angle $\alpha$ is selected so that the number of reflections of radiation propagating along the waveguide is from the range 10 to 30.

78. The absorbance cell of claim 76 in which the angle $\alpha$ is greater than 2°.

79. The absorbance cell of claim 78 in which the first reflecting element is coated with the electrically non-conducting material.

80. The absorbance cell of claim 78 in which the second reflecting element is formed on the channel facing surface of the top plate.

81. The absorbance cell of claim 80 in which the second reflecting element is coated with the electrically non-conducting material.

82. The absorbance cell of claim 76 in which the angle $\alpha$ is selected so that the number of reflections of radiation propagating along the waveguide is greater than 4.

83. The absorbance cell of claim 69 in which the waveguide input end is arranged such that radiation introduced to the waveguide has a free space mode of propagation.

84. The absorbance cell of claim 69 in which the reflecting elements extend laterally to form a shield between a measuring radiation source and a measuring radiation detector.

85. The absorbance cell of claim 69 further comprising:

a detector of radiation exiting the radiation output end, the detector having a detection region; and at least one of the reflecting elements extending laterally to cover the detection region of the detector.

86. The absorbance cell of claim 85 in which the at least one of the reflecting elements extends laterally more than a millimeter.

87. The absorbance cell of claim 85 in which the reflecting elements are square.

88. The absorbance cell of claim 69 in which the channel is coated with polysiloxane.

89. The absorbance cell of claim 69 in which the fluid inlet comprises:

a flat ended capillary inserted through a hole in the top plate, with the flat ended capillary butting up against the channel bearing surface of the bottom plate, the channel having a depth, width and length longer than the width, and with the flat ended capillary centered over the width of the channel.

90. The absorbance cell of claim 69 in which the channel has a depth from 10 to 30 $\mu$m.

91. The absorbance cell of claim 69 in which the first reflecting element is formed on the channel bearing surface of the bottom plate.

* * * * *

UNITED STATES PATENT AND TRADEMARK OFFICE
CERTIFICATE OF CORRECTION

PATENT NO.    : 6,224,830 B1
DATED         : May 1, 2001
INVENTOR(S)   : D.J. Harrison et al.

It is certified that error appears in the above-identified patent and that said Letters Patent is hereby corrected as shown below:

Title page,
Item [75], Inventors, "Edmonton;" should read -- Edmonton (CA); -- "Beaumont;" should read -- Edmonton (CA); -- "Edmonton;" should read -- San Mateo, CA (US); -- "Edmonton;" should read -- Mannheim, Germany; -- "Edmonton;" should read -- Mountain View, CA (US); -- "Edmonton, all of (CA)" should read -- Red Deer, (CA) --

Item [56], References Cited, "absoprtion" should read -- absorption -- "Chromatograhy," should read -- Chromatography, --

Column 13,
Line 29, "fiat" should read -- flat --
Line 51, "claim 1" should read -- claim 8, --

Signed and Sealed this

Eighth Day of January, 2002

*Attest:*

JAMES E. ROGAN
*Attesting Officer*   *Director of the United States Patent and Trademark Office*